United States Patent
Miyasato (10) Patent No.: US 9,433,355 B2
(45) Date of Patent: Sep. 6, 2016

(54) PHOTOACOUSTIC IMAGING APPARATUS AND PHOTOACOUSTIC IMAGING METHOD (75) Inventor: Takuro Miyasato, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 364 days.

(21) Appl. No.: 13/634,741

(22) PCT Filed: Apr. 19, 2011

(86) PCT No.: PCT/JP2011/060004
§ 371 (c)(1),
(2), (4) Date: Sep. 13, 2012

(87) PCT Pub. No.: WO2011/136153
PCT Pub. Date: Nov. 3, 2011

(65) Prior Publication Data
US 2013/0006090 A1 Jan. 3, 2013

(30) Foreign Application Priority Data
Apr. 28, 2010 (JP) ................. 2010-104300

(51) Int. Cl.
A61B 5/05 (2006.01)
A61B 5/00 (2006.01)

(52) U.S. Cl.
CPC ........... A61B 5/0095 (2013.01); A61B 5/0091 (2013.01); A61B 5/4312 (2013.01)

(58) Field of Classification Search
CPC ................... A61B 5/4312; A61B 5/0095
See application file for complete search history.

(56) References Cited

U.S. PATENT DOCUMENTS

2008/0186480 A1 8/2008 Lang et al.
2008/0221647 A1* 9/2008 Chamberland et al. ........ 607/88
(Continued)

FOREIGN PATENT DOCUMENTS

JP 2008-191160 A 8/2008
JP 2008-307372 A 12/2008
(Continued)

OTHER PUBLICATIONS

Oraevsky et al.,"Measurement of tissue optical properties by time-resolved detection of laser-induced transient stress" Applied Optics, Jan. 1997, pp. 402-415, vol. 36, No. 1.
(Continued)

Primary Examiner — Jonathan Cwern
Assistant Examiner — Amelie R Gillman
(74) Attorney, Agent, or Firm — Canon U.S.A. Inc., IP Division (57) ABSTRACT A photoacoustic imaging apparatus includes holding members configured to hold a subject, an acoustic wave conversion unit configured to receive an acoustic wave generated by irradiating the subject, which is held by the holding members, with light from a light source and convert the acoustic wave into an electric signal, a processing unit configured to generate image data from the electric signal, and an imaging unit configured to capture an optical pattern generated on a light diffusion member by emitting the light to the light diffusion member arranged on a surface of a side where the subject is irradiated with the light in the holding members where the holding members contact the subject in holding the subject, wherein the processing unit calculates light absorption coefficient distribution in the subject based on the optical pattern captured by the imaging unit and the electric signal acquired by the acoustic wave conversion unit.

13 Claims, 9 Drawing Sheets

(56) References Cited

U.S. PATENT DOCUMENTS

2009/0005685 A1* 1/2009 Nagae et al. .................. 600/459
2010/0053618 A1* 3/2010 Nakajima et al. ............. 356/432
2012/0002193 A1* 1/2012 Elliott et al. .................. 356/121

FOREIGN PATENT DOCUMENTS

| JP | 200918153 A | 1/2009 |
| JP | 2010-088627 A | 4/2010 |
| JP | 2010-088873 A | 4/2010 |

OTHER PUBLICATIONS

Laufer et al.,"Quantitative spatially resolved measurement of tissue chromophore concentrations using photoacoustic spectroscopy" Physics in Medicine and Biology, 2007, pp. 141-168, vol. 52.

* cited by examiner

PHOTOACOUSTIC IMAGING APPARATUS AND PHOTOACOUSTIC IMAGING METHOD

TECHNICAL FIELD

The present invention relates to a photoacoustic imaging apparatus and a photoacoustic imaging method.

BACKGROUND ART

Researches on imaging apparatuses for transmitting light emitted from a light source such as a laser to a subject in the body of the subject and acquiring information of the inside of the subject has been actively done mainly in the medical field. In such imaging techniques, photoacoustic tomography (PAT) has been proposed.

The PAT is a technology for visualizing information relating to optical characteristics of the inside of a living body (i.e., a subject). In the PAT, the living body (subject) is irradiated with pulse light generated from a light source, an acoustic wave generated by the light transmitted and diffused in the living body and absorbed by the body tissue is received, and the received acoustic wave is analyzed and processed. By the PAT, information of the living body such as optical characteristic value distribution in the subject, especially, light energy absorption density distribution can be acquired.

In the PAT, an initial sound pressure $P_0$ of the acoustic wave generated from the light absorber in the subject can be expressed by the following expression:

$$P_0 = \Gamma \cdot \mu_a \cdot \Phi \qquad \text{expression 1}$$

where $\Gamma$ is a Gruneisen coefficient. The Gruneisen coefficient is obtained by dividing the product of a coefficient of volumetric expansion $\beta$ and the squared sound speed c by the specific heat at constant pressure $C_p$. It is known that the coefficient $\Gamma$ takes a substantially constant value if the subject is specified. $\mu_a$ is a light absorption coefficient, and $\Phi$ is a light amount (light amount emitted to an absorber, and also referred to as light influence) in a local region.

Time change of the sound pressure P that is a level of an acoustic wave transmitted inside the subject is measured, and based on the measurement result, initial sound pressure distribution is calculated. The calculated initial sound pressure distribution is divided by the Gruneisen coefficient $\Gamma$ to obtain distribution of the products of $\mu_a$ and $\Phi$, that is, light energy absorption density distribution.

As shown in the expression 1, in order to obtain the distribution of the light absorption coefficient $\mu_a$ from the distribution of the initial sound pressure $P_0$, it is necessary to obtain the distribution of the light amount $\Phi$ in the subject. If it is assumed that when a region large enough to the thickness of the subject is evenly irradiated with light of a certain level, the light transmits inside the subject like a plane wave, the distribution $\Phi$ of the light amount in the subject can be expressed as follows:

$$\Phi = \Phi_0 \cdot \exp(-\mu_{\mathit{eff}} \cdot d) \qquad \text{expression 2}$$

where, $\mu_{\mathit{eff}}$ is an average equivalent damping coefficient of the subject, and $\Phi_0$ is the amount (light amount on a surface of the subject) of the light that enters in the subject from the light source. Moreover, d is a distance from the region (light irradiation region) on the surface of the subject irradiated with the light from the light source to the light absorber in the subject.

According to patent document 1, a living body is evenly irradiated with light under a plurality of conditions, an average equivalent damping coefficient $\mu_{\mathit{eff}}$ of the subject is calculated, light amount distribution $\Phi$ in the subject is calculated by the expression 2, and using the light amount distribution $\Phi$, light absorption coefficient distribution $\mu_a$ in the subject can be obtained by the expression 1.

CITATION LIST PATENT LITERATURE

Japanese Patent Application Laid-Open No. 2009-18153

Summary of Invention Technical Problem

However, if the amount of the light emitted from the light source to the subject is uneven, the light irradiation density distribution on the surface of the subject is uneven too. Accordingly, the light amount distribution in the subject is uneven in the in-plane direction to the irradiated surface. Then, the expression 2 cannot be used. Accordingly, in order to accurately obtain the light absorption coefficient distribution in the subject, the uneven characters must be taken into consideration.

Solution to Problem

According to an aspect of the present invention, a photoacoustic imaging apparatus having holding members configured to hold a subject, an acoustic wave conversion unit configured to receive an acoustic wave generated by irradiating the subject being held with light from a light source and convert into an electric signal, and a processing unit configured to generate image data from the electric signal is provided. The photoacoustic imaging apparatus includes an imaging unit configured to capture an optical pattern generated on a light diffusion member by emitting the light to the light diffusion member arranged on a surface of a side where the subject is irradiated with the light in the surfaces of the holding members where the holding members and the subject come in contact with each other in holding the subject. The processing unit calculates light absorption coefficient distribution in the subject using the optical pattern captured by the imaging unit and the electric signal acquired by the acoustic wave conversion unit.

According to an aspect of the present invention, a photoacoustic imaging apparatus having holding members configured to hold a subject, an acoustic wave conversion unit configured to receive an acoustic wave generated by irradiating the subject being held with light from a light source and convert into an electric signal, and a processing unit configured to generate image data from the electric signal is provided. The photoacoustic imaging apparatus includes an imaging unit configured to capture an optical pattern generated on a light diffusion member by emitting the light to the light diffusion member arranged on a surface of a side where the subject is irradiated with the light in the surfaces of the holding members where the holding members and the subject come in contact with each other in holding the subject. The processing unit calculates light irradiation density distribution of the light emitted to the subject using the optical pattern captured by the imaging unit.

According to an aspect of the present invention, a photoacoustic imaging method for holding a subject by holding members, receiving an acoustic wave generated by irradiating the subject being held with light from a light source and converting into an electric signal, and generating image data from the electric signal is provided. The photoacoustic imaging method includes capturing an optical pattern generated on a light diffusion member by emitting the light to the light diffusion member arranged on a surface of a side where the subject is irradiated with the light in the surfaces of the holding members where the holding members and the subject come in contact with each other in holding the subject, and calculating light absorption coefficient distribution in the subject using the captured optical pattern and the acquired electric signal.

According to an aspect of the present invention, a photoacoustic imaging method for holding a subject by holding members, receiving an acoustic wave generated by irradiating the subject being held with light from a light source and converting into an electric signal, and generating image data from the electric signal is provided. The photoacoustic imaging method includes capturing an optical pattern generated on a light diffusion member by emitting the light to the light diffusion member arranged on a surface of a side where the subject is irradiated with the light in the surfaces of the holding members where the holding members and the subject come in contact with each other in holding the subject, and calculating light irradiation density distribution of the light emitted to the subject using the optical pattern captured by the imaging unit.

Advantageous Effects of Invention

According to the present invention, light characteristic value distribution in a subject, especially, light absorption coefficient distribution can be accurately obtained.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

FIG. 7 (7A and 7B) is a flowchart illustrating an example operation of a photoacoustic imaging apparatus according to a fourth exemplary embodiment of the present invention.

DESCRIPTION OF EMBODIMENTS

Various exemplary embodiments, features, and aspects of the invention will be described in detail below with reference to the drawings.

In the exemplary embodiments of the present invention, acoustic waves include a sound wave, an ultrasonic wave, and a photoacoustic wave, and are elastic waves generated by irradiating a subject with light (electromagnetic wave) such as near infrared rays. A photoacoustic imaging apparatus according to the present invention is directed to an apparatus that acquires biometric information of the inside of a subject and generates image data mainly for diagnosing malignacy, blood vessel disease, and the like of humans or animals and for a follow-up of chemical treatment.

Accordingly, it is expected that the subject is a living body, more specifically, the subject can be a target part for diagnosis such as a breast, a finger, or a limb of a human or an animal. A light absorber of the inside of the subject has a relatively high light absorption coefficient in the subject, for example, if the measurement target is a human body, the light absorber can be oxygenated or reduced hemoglobin, a blood vessel including the oxygenated or reduced hemoglobin, or a malignacy including many new blood vessels.

Example 1

Figure 1A:
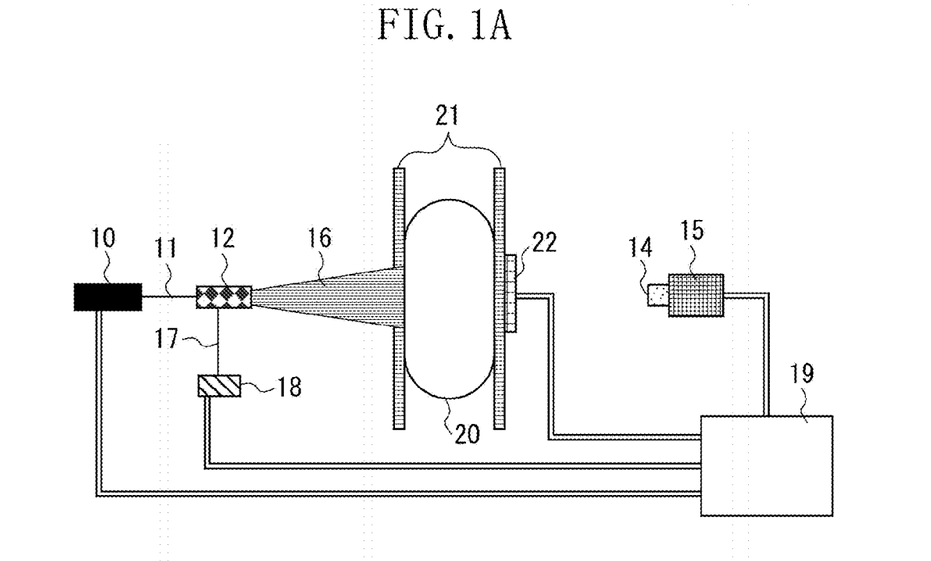
FIGS. 1A and 1B are schematic views illustrating an example configuration of a photoacoustic imaging apparatus according to a first exemplary embodiment of the present invention.
Figure 1B:
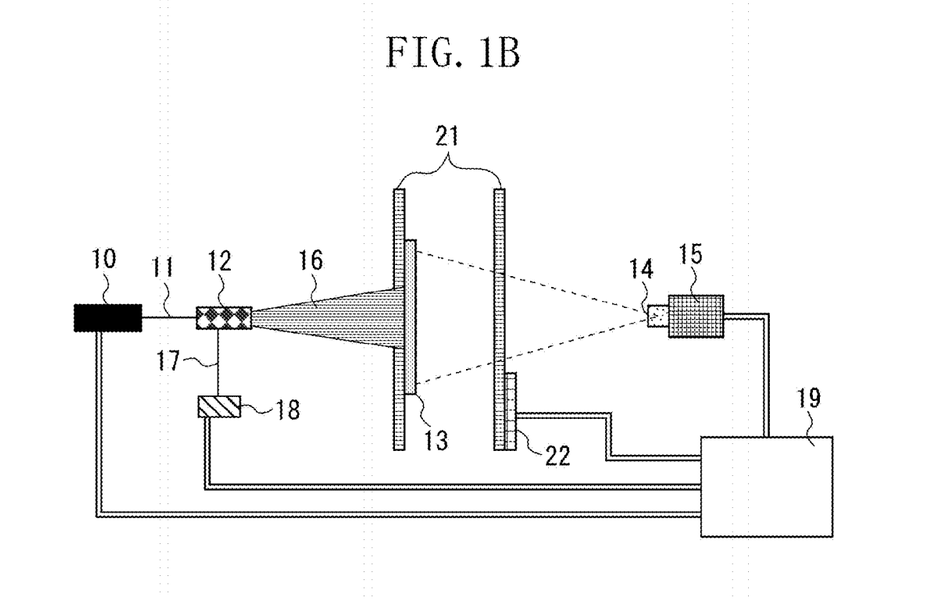

FIG. 1 illustrates a configuration of the photoacoustic imaging apparatus according to the present exemplary embodiment. The photoacoustic imaging apparatus according to the present exemplary embodiment includes holding members 21, an acoustic wave conversion unit 22, and a processing unit 19. The holding members 21 can be moved to hold a subject 20 at a predetermined position.

Referring to FIG. 1A, PAT measurement performed using the photoacoustic imaging apparatus according to the present exemplary embodiment is described. Light 11 emitted from a light source 10 travels through an optical system 12 including, for example, a lens, a mirror, and an optical fiber, onto the subject 20 such as a living body. Preferably, the optical system 12 includes a magnifying lens for magnifying an irradiated field of the light 11. By the magnification lens, the light 11 is changed to light 16, and emitted to the subject 20.

A part of the energy of the light transmitted inside the subject 20 is absorbed by a light absorber (serves as a sound source as a result) in a blood vessel or in blood. Then, due to thermal expansion of the light absorber, an acoustic wave (typically, ultrasonic wave) is generated. The acoustic wave is received by the acoustic wave conversion unit 22, and converted into an electric signal.

The processing unit 19 generates image data of light absorption coefficient distribution in the subject 20 using initial sound pressure distribution in the subject 20 acquired from the electric signal and light amount distribution in the subject 20. The image data is displayed on a display device (not illustrated) such as a liquid crystal display as an image.

The light amount distribution in the subject 20 is calculated using relative light irradiation density distribution of the light emitted on the surface of the subject 20. The relative light irradiation density distribution is relative light intensity distribution in a light irradiation region on the surface of the subject 20. The relative light irradiation density distribution can be obtained by irradiating a light diffusion member 13 (FIG. 1B) arranged on a surface of a side where the subject 20 is to be irradiated with the light of the surfaces of the holding members 21 where the holding members 21 and the subject 20 are in contact with each other when the subject 20 is held, and by capturing an optical pattern (diffusion light pattern) generated on the surface of the light diffusion member 13.

Specifically, the relative light irradiation density distribution is calculated by analyzing the captured optical pattern by the processing unit. For the purpose, the photoacoustic imaging apparatus according to the present exemplary embodiment includes an imaging unit 15. As illustrated in FIG. 1B, in a state where the subject 20 is not being held by the holding members 21, and the light diffusion member 13 is placed on the side (side nearer to the light source) to be irradiated with the light, of the two planes of the two holding members 21 face to each other, the light diffusion member 13 is irradiated with the light from the light source 10.

Then, an optical pattern generated on the light diffusion member 13 is captured by the imaging unit 15. In the imaging unit 15, an optical system 14 such as a neutral density (ND) filter, a lens, and the like are arranged. The lens has a focal length enough for the imaging unit 15 to capture an image of the entire optical pattern of irradiation light 16 diffused on the light diffusion member 13. The ND filter has ND sufficient for the imaging unit 15 to capture the entire optical pattern of the irradiation light 16 diffused on the light diffusion member 13.

In capturing the optical pattern, the acoustic wave conversion unit 22 is arranged at a position not interfering with the image capturing. For this purpose, the acoustic wave conversion unit 22 is configured to be movable. Specifically, a scanning mechanism for scanning along the plane on which the subject 20 is not to be held between the holding members 21, is provided. The processing unit 19 is interconnected with the acoustic wave conversion unit 22, the light source 10, and a light amount measurement unit 18 by wires, or the like so that data or an instruction can be transmitted or received.

The optical system 12 includes an optical system for splitting the light 11 into the irradiation light 16 for irradiating the holding members 21 and reference light 17 for irradiating the light amount measurement unit 18 that measures the light amount, for example, a half mirror. The ratio of the irradiation light 16 and the reference light 17 can be adjusted by the half mirror, or the like in advance.

With this configuration, by measuring the light amount of the reference light 17 by the light amount measurement unit 18, the total light amount of the irradiation light 16 can be acquired. The acquisition of the total light amount of the irradiation light 16 is performed for the following reason. That is, the relative light irradiation density distribution only indicates relative intensity in the distribution, and does not contain information of absolute intensity. Accordingly, in order to obtain light irradiation density distribution containing the information of the absolute intensity, it is necessary to acquire information of the total light amount in the relative light irradiation density distribution.

The light amount measurement unit 18 is not always necessary, but the optical system 12 can employ an optical system for transmitting only a desired amount of the light or a ratio set at the time of manufacturing the photoacoustic imaging apparatus can be used.

Figure 2:
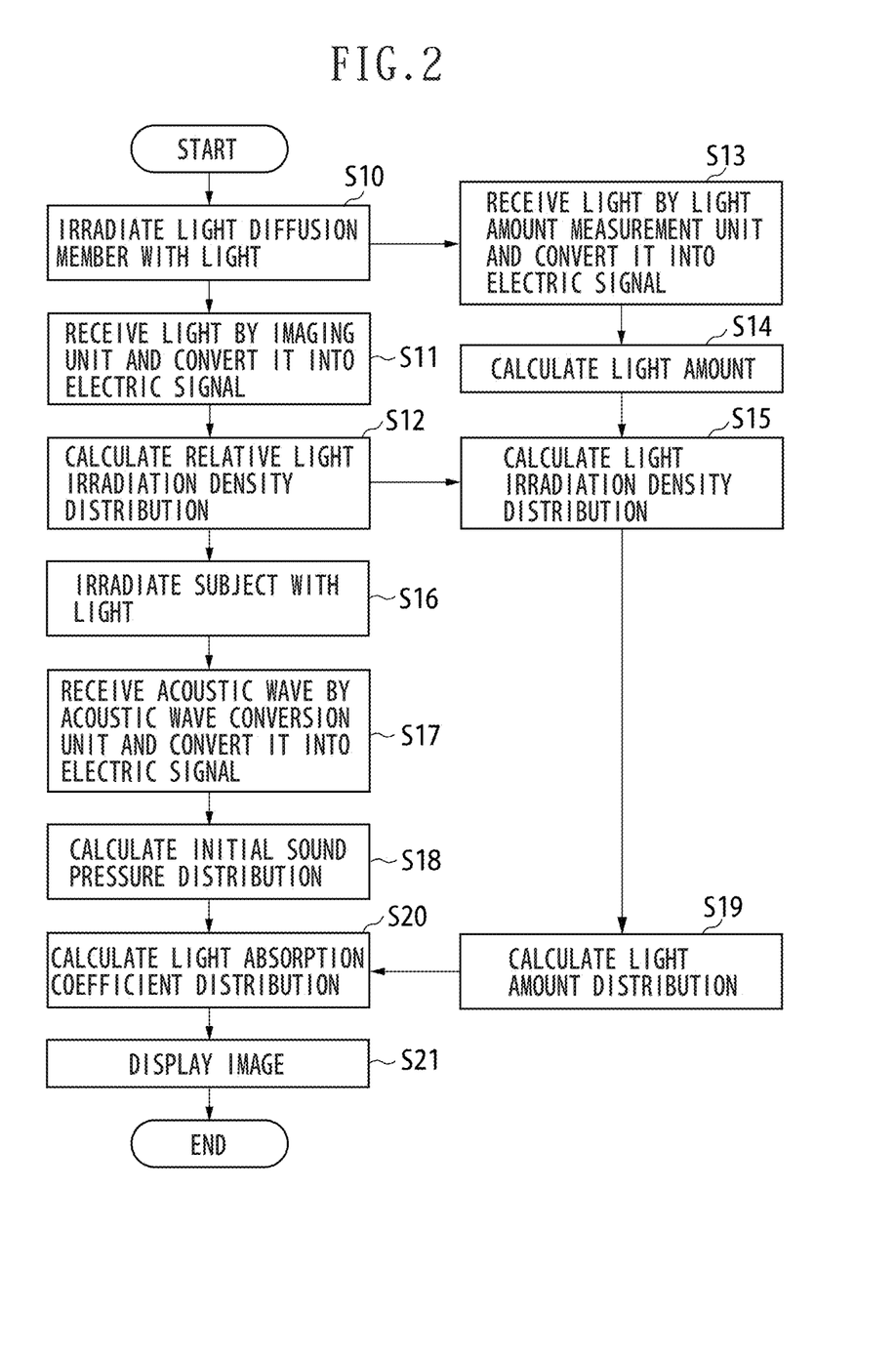
FIG. 2 is a flowchart illustrating an example operation of the photoacoustic imaging apparatus according to the first exemplary embodiment of the present invention.

The operation of the biometric information optical imaging apparatus according to the present exemplary embodiment will be described with reference to FIG. 2. First, as illustrated in FIG. 1B, in step S10, instead of placing the subject 20 in the holding members 21, the light diffusion member 13 is arranged to contact the side of the holding member 21 that is irradiated with the irradiation light 16. In step S10, the light diffusion member 13 is irradiated with the irradiation light 16 that is the light 11 emitted from the light source 10 and traveled through the optical system 12.

The irradiation light 16 emitted to the light diffusion member 13 is diffused on the light diffusion member 13. In step S11, the diffusion light pattern is received on the imaging unit 15 through the optical system 14, and converted into a first electric signal. The first electric signal is transmitted to the processing unit 19. The first electric signal is required to have a value in proportion to the light amount. That is, to the electric signal, nonlinear gain that indicates that its gamma value is a value other than one must not be applied.

Figure 3:
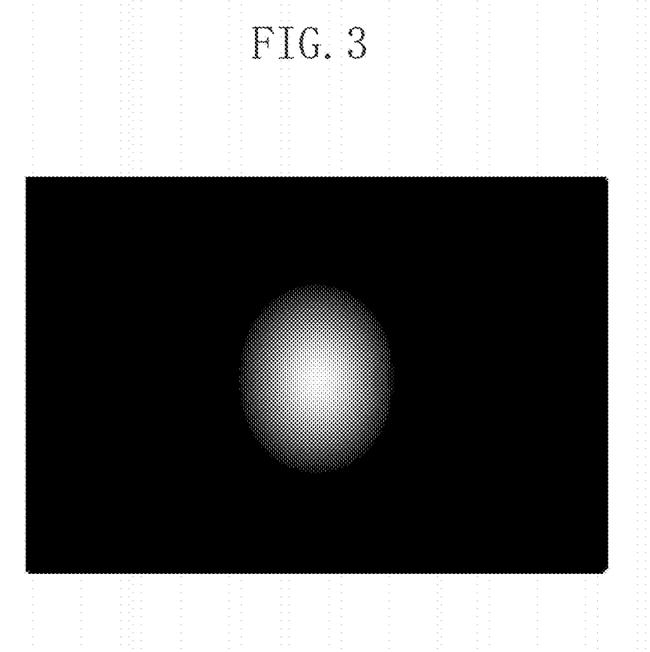
FIG. 3 illustrates relative light irradiation density distribution captured by the photoacoustic imaging apparatus according to the first exemplary embodiment of the present invention.

In step S12, the processing unit 19 calculates relative light irradiation density distribution on the light diffusion member 13 from the first electric signal. Specifically, the relative light irradiation density distribution is calculated using the diffusion light pattern captured by the imaging unit 15 and the size of the imaging target (in the exemplary example, the light diffusion member 13) per one pixel measured in advance. The diffusion light pattern captured by the imaging unit 15 is illustrated in FIG. 3.

In step S13, the reference light 17 split by the optical system 12 from the irradiation light 16 is received by the light amount measurement unit 18, and converted into a second electric signal. In step S14, the second electric signal is transmitted to the processing unit 19, and the amount of the reference light 17 is calculated. The light amount of the reference light 17 and the light amount of the irradiation light 16 are adjusted to a predetermined ratio, or the ratio is measured in advance. Accordingly, the processing unit 19 calculates the total light amount of the irradiation light 16 from the light amount of the reference light 17.

In step S15, from the total light amount of the irradiation light 16 and the relative light irradiation density distribution, the processing unit 19 calculates light irradiation density distribution on the light diffusion member 13. It is estimated that the light irradiation density distribution is similar to the light irradiation density distribution on the surface of the subject 20 as long as substantially the same electric power is supplied to the light source 10 in irradiating the light diffusion member 13 with the light and in irradiating the subject 20 with the light.

In step S16, as illustrated in FIG. 1A, in a state that the holding members 21 hold the subject 20 and the acoustic wave conversion unit 22 is arranged at a position opposing the surface on the subject 20 to be irradiated with the irradiation light 16, the subject 20 is irradiated with the irradiation light 16 from the light source 10.

A part of the light energy of the irradiation light 16 is absorbed by a light absorber in the subject 20, and an acoustic wave is generated. In step S17, the acoustic wave conversion unit 22 receives the generated acoustic wave and converts it into a second electric signal. In step S18, the second electric signal is transmitted to the processing unit 19, and the processing unit 19 analyzes the second electric signal, and calculates initial sound pressure distribution.

In step S19, based on the light irradiation density distribution calculated in step S15, the processing unit 19 calculates light amount distribution in the subject 20. Specifically, on the surface of the subject in the calculation space, a virtual light source having light irradiation density distribution similar to the above-mentioned light irradiation density distribution is arranged, and using a light diffusion equation, a transport equation, Monte Carlo light transport simulation, or the like, the light amount distribution is calculated.

Figure 4A:
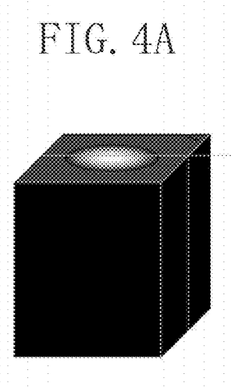
FIGS. 4A to 4D illustrate a part of the operation of the photoacoustic imaging apparatus according to the first exemplary embodiment of the present invention.
Figure 4B:
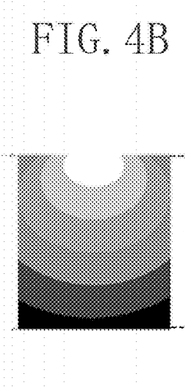

FIG. 4A is a conceptual diagram illustrating the virtual light source arranged on the surface of the subject in the calculation space. A view from the top surface corresponds to the relative light irradiation density distribution in FIG. 3. FIG. 4B is a cross-sectional view of the calculated light amount distribution.

Figure 4C:
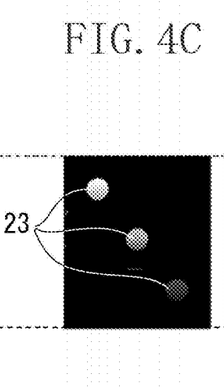
Figure 4D:
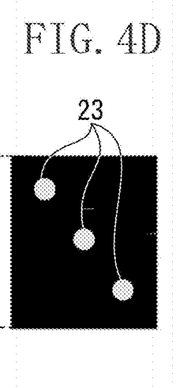

In step S20, the processing unit 19 calculates light absorption coefficient distribution using the initial sound pressure distribution calculated in step S18 and the light amount distribution calculated in step S19. Specifically, according to the expression 1, by dividing the initial sound pressure distribution (its image corresponds to FIG. 4C) by the light amount distribution (its image corresponds to FIG. 4B), the light absorption coefficient distribution (its image corresponds to FIG. 4D) is calculated. Reference numeral 23 in FIGS. 4C and 4D denotes light absorbers.

Finally, the processing unit 19 generates image data of the light absorption coefficient distribution calculated in step S20. In step S21, the image data is displayed by a display device (not illustrated).

As described above, the light amount distribution of the subject can be obtained more accurately by estimating the light irradiation density distribution using the light diffusion member. Accordingly, the light absorption coefficient distribution can be accurately obtained.

The configuration of the photoacoustic imaging apparatus according to the present exemplary embodiment will be specifically described below. The light source emits light of a certain wavelength to be absorbed by a certain component (for example, hemoglobin) of a living body. More specifically, the wavelength of the light is preferably greater than or equal to 500 nm and less than or equal to 1200 nm. The light source has at least one light source that can generate pulsed light of 5 to 50 nanoseconds.

Preferably, the light source is a laser that has large output, but instead of the laser, a light-emitting diode, or the like can be used. Examples of the laser include various lasers such as solid-state lasers, gas lasers, dye lasers, and semiconductor lasers. Nd:YAG laser or Ti:sapphire laser can also be used. The lasers can be wavelength-variable lasers.

The optical system includes, for example, a mirror for reflecting light, a half mirror for splitting light into reference light and irradiation light, a lens for focusing light, magnifying light, or changing a shape of light, or the like. Examples of such an optical system include, other than the mirrors and the lenses, optical waveguides, and any component can be employed as long as the component can deliver light emitted from a light source in a desired shape to a subject.

Preferably, the light is spread to an area of a certain size by diffusing the light with a lens. Further, preferably, the area to be irradiated with the light on the subject can be moved on the subject. In other words, preferably, the apparatus is configured in such a manner that the light emitted from the light source can be moved on the subject. With the light being movable, a wider area can be irradiated with the light.

Examples of the method for moving the area on the subject to be irradiated with the light include a method of using a movable mirror, and a method for mechanically moving the light source itself. The light source can be integrated with the holding members.

The light amount measurement unit is an optical power meter. Examples of the light amount measurement unit include an optical sensor using a photodiode, a thermal sensor using a thermocouple element, and a pyroelectric sensor using a pyroelectric. Since the light source according to the present exemplary embodiment uses a single pulse, the use of the pyroelectric sensor is preferable.

Preferably, the light diffusion member is a scattering member, a diffuser panel, a thin urethane sheet that contains titanium oxide, or the like. Moreover, preferably, the light diffusion member has a diffusion angle uniform in a plane in isotropic circle diffusion, and the diffusion angle is sufficiently wider than angles of view of the imaging unit and the lens. For example, if the angle of view is 20 degrees, preferably, the light diffusion member has a diffusion angle of 60 degrees or more so that the intensity of the diffusion light does not vary within the angle of ±10 degrees of the angle of view.

The light diffusion member may be removable, or may be integrated with the holding members. The thickness of the light diffusion member ranges, preferably, from 0.1 mm to 1.0 mm.

The imaging unit has at least one element for detecting light and converting the light into an electric signal. The imaging unit includes a photomultiplier tube, a photodiode, and the like. As long as light is detected and the light is converted into an electric signal, any element can be used.

By arranging the elements for detecting light in a plurality of one-dimensional or two-dimensional arrays, the light can be simultaneously detected at a plurality of positions, thereby detection time can be reduced. By moving one element, a signal similar to the signal obtained by arranging the plurality of elements in two-dimensional or one-dimensional arrays can be obtained. It is required that the element has sensitivity to the wavelength range of the light to be emitted.

The acoustic wave conversion unit has at least one element for receiving an acoustic wave and converting the acoustic wave into an electric signal. The acoustic wave conversion unit can include a transducer using a piezoelectric phenomenon, a transducer using optical resonance, a transducer using change in capacitance, or the like. As long as an acoustic wave is received and the acoustic wave is converted into an electric signal, any element can be used.

By arranging the elements for receiving an acoustic wave in a plurality of one-dimensional or two-dimensional arrays, the acoustic wave can be simultaneously received at a plurality of positions, thereby reception time can be reduced and effects such as oscillation of a subject can be reduced. By moving one element, a signal similar to the signal obtained by arranging the plurality of elements in two-dimensional or one-dimensional arrays can be obtained.

Typically, the processing unit is a workstation. In the processing unit, light irradiation density distribution is calculated and processing for feeding back the result to the irradiation light, and the like is performed by preprogrammed software. The processing unit also performs noise reduction processing, or the like onto an electric signal transmitted from the acoustic wave conversion unit.

The holding members include a container or two flat plates to hold a subject. In a case where the holding members are two flat plates, at least one of the two plates can be moved. In PAT measurement, the one plate can be moved to hold the subject. Preferably, the subject contains a material having acoustic impedance near a human breast, or the like such as a polymethylpentene polymer.

Example 2

A photoacoustic imaging apparatus according to a second exemplary embodiment has a configuration similar to that in the first exemplary embodiment. In the present exemplary embodiment, in order to obtain light absorption coefficient distribution more accurately, in PAT measurement, a light amount of the light source is calculated, and using the value, light irradiation density distribution is calculated. That is, in the first exemplary embodiment, the light irradiation density distribution is calculated from the light amount when the light diffusion member is irradiated with the light. However, in the present exemplary embodiment, the light irradiation density distribution is calculated from a light amount when the subject is irradiated with the light.

Figure 5:
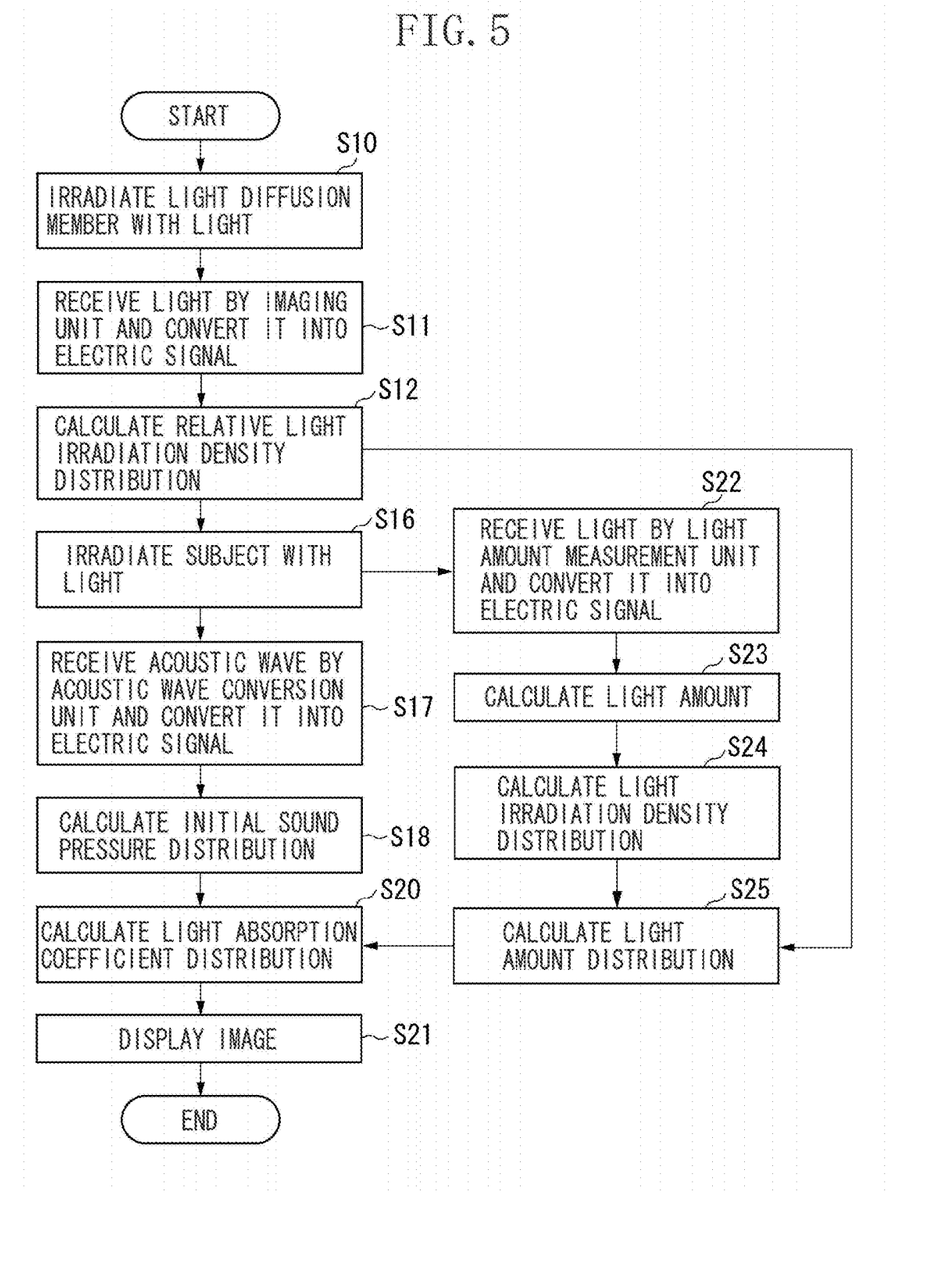
FIG. 5 is a flowchart illustrating an example operation of a photoacoustic imaging apparatus according to a second exemplary embodiment of the present invention.

The operation of the photoacoustic imaging apparatus according to the present exemplary embodiment will be described below with reference to FIG. 5. First, the processing from steps S10 to S12 is performed similarly to the first exemplary embodiment.

In step S16, as illustrated in FIG. 1A, in a state where the holding members 21 hold the subject 20 and the acoustic wave conversion unit 22 is arranged at a position opposing the surface on the subject 20 to be irradiated with the irradiation light 16, the subject 20 is irradiated with the irradiation light 16 from the light source 10. The processing in steps S17 and S18 is performed also similarly to the first exemplary embodiment.

Meanwhile, as illustrated in FIG. 1B, in step S22, a part of the light 11 (reference light 17) that is split from the irradiation light 16 that irradiates the subject 20 in step S16 is received by the light amount measurement unit 18, and the reference light 17 is converted into an electric signal. In step S23, the electric signal is transmitted to the processing unit 19, and the amount of the reference light 17 is calculated.

The light amount of the reference light 17 and the light amount of the irradiation light 16 are adjusted to a predetermined ratio, or the ratio is measured in advance. Accordingly, the processing unit 19 calculates the total light amount of the irradiation light 16 from the light amount of the reference light 17.

In step S24, from the total light amount of the irradiation light 16 and the relative light irradiation density distribution, the processing unit 19 calculates light irradiation density distribution on the surface of the subject 20. In step S25, similarly to the above-described processing in step S19 in the first exemplary embodiment, the processing unit 19 calculates light amount distribution in the subject 20 using the light irradiation density distribution.

In step S20, the processing unit 19 calculates light absorption coefficient distribution using the initial sound pressure distribution calculated in step S18 and the light amount distribution calculated in step S25. Finally, the processing unit 19 generates image data using the light absorption coefficient distribution calculated in step S20. In step S21, the image data is displayed by a display device (not illustrated).

Example 3

A third exemplary embodiment is similar to the photoacoustic imaging apparatus according to the first exemplary embodiment. However, in the present exemplary embodiment, the light source is a laser generator for safety reasons in a case where the subject is a human. More specifically, before PAT measurement, it is determined whether a maximum value of light irradiation density distribution of emitted light is less than or equal to a maximum permissible exposure (MPE) that can be emitted on a surface of a living body. If the maximum value of the light irradiation density distribution exceeds the MPE, adjustment of the light output is performed.

One of standards defining the MPE is 60825-1 "SAFETY OF LASER PRODUCTS—Part 1: Equipment classification, requirements and user's guide" prepared by the International Electro-technical Commission (IEC). Also, there is a standard in JIS C 6802 "Safety of laser products" of Japanese Industrial Standards (JIS), which conforms to IEC.

Figure 6:
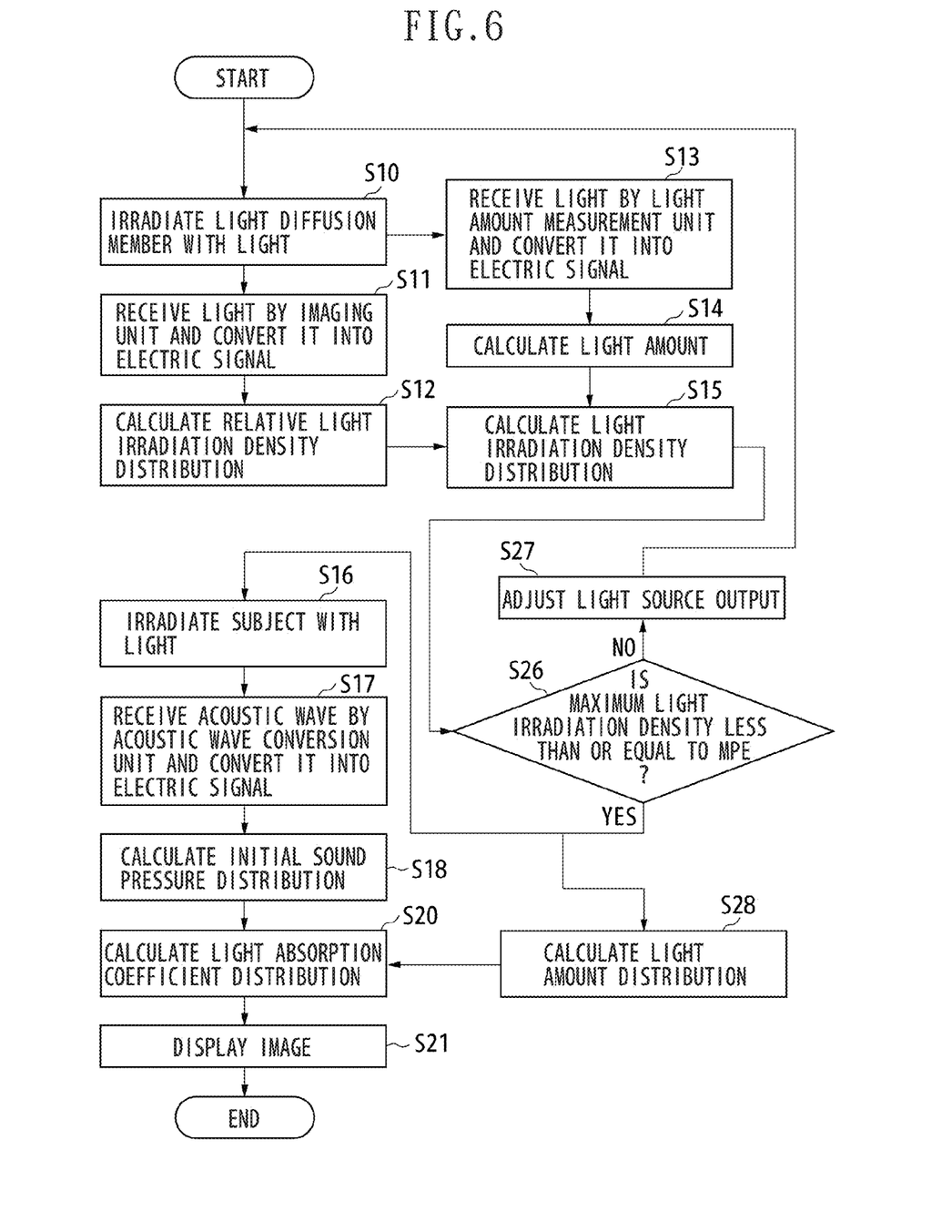
FIG. 6 is a flowchart illustrating an example operation of a photoacoustic imaging apparatus according to a third exemplary embodiment of the present invention.

Referring to FIG. 6, the operation of the photoacoustic imaging apparatus according to the present exemplary embodiment will be described. First, the processing from step S10 to S15 is performed similarly to that in the first exemplary embodiment.

In step S26, whether the maximum value (maximum light irradiation density) in the light irradiation density distribution calculated in step S15 is less than or equal to the above-mentioned maximum permissible exposure (MPE) is determined. If the maximum light irradiation density exceeds the MPE (NO in step S26), in step S27, the output energy of the light source 10 is adjusted.

Specifically, the input electric power to a pumping lamp of the light source (laser) is decreased by a desired value (for example, 0.5 J). For this purpose, the processing unit 19 has a control unit for controlling the output energy of the light emitted to the subject 20. Using the adjusted light source 10, the processing from steps S10 to step S15 is sequentially performed, and in step S26, whether the maximum light irradiation density is less than or equal to the MPE is determined again. Until the maximum light irradiation density becomes less than or equal to the MPE, the processing of step S27 and the processing from steps S10 to step S26 is sequentially repeated.

In step S26, if it is determined that the maximum light irradiation density is less than or equal to the MPE (YES in step S26), the light is emitted to the subject 20, and the processing from steps S16 to step S18 described in the first exemplary embodiment is performed.

Then, processing of step S20 is performed. The light amount distribution to be used in this step is calculated in step S28 using the light irradiation density distribution when it is determined that the maximum light irradiation density is less than or equal to the MPE in step S26. Finally, in step S21, the processing unit 19 generates image data of the light absorption coefficient distribution calculated in step S20. The image data is displayed by a display device (not illustrated).

Instead of the step of determining whether the maximum light irradiation density is less than or equal to the MPE in step S26, the processing unit 19 can determine whether the maximum light irradiation density in step S26 is less than or equal to the MPE and the maximum light irradiation density is greater than or equal to a predetermined value (for example, a half value of the MPE). In such a case, it can be prevented that the intensity of the light to be emitted to the subject 20 becomes so small that the light cannot travel to a deep part of the subject 20.

In step S27, if the maximum light irradiation density exceeds the MPE, the output of the light source 10 is adjusted so that the input electric power is decreased by a desired value (for example, 0.5 J), and if the maximum light irradiation density does not exceed the predetermined value, the output of the light source 10 is adjusted so that the input electric power is increased by a desired value (for example, 0.5 J). Until the maximum light irradiation density becomes less than or equal to the MPE, and the maximum light irradiation density becomes greater than or equal to a predetermined value (for example, a half value of the MPE), the processing of step S27 and the processing from step S10 to step S26 is sequentially repeated.

Example 4

An photoacoustic imaging apparatus according to a fourth exemplary embodiment has a configuration similar to that in the third exemplary embodiment (that is, the configuration similar to that in the first exemplary embodiment). However, in the present exemplary embodiment, similar to the second exemplary embodiment, in PAT measurement, a light amount of the light source is calculated.

Figures 7, 7A:
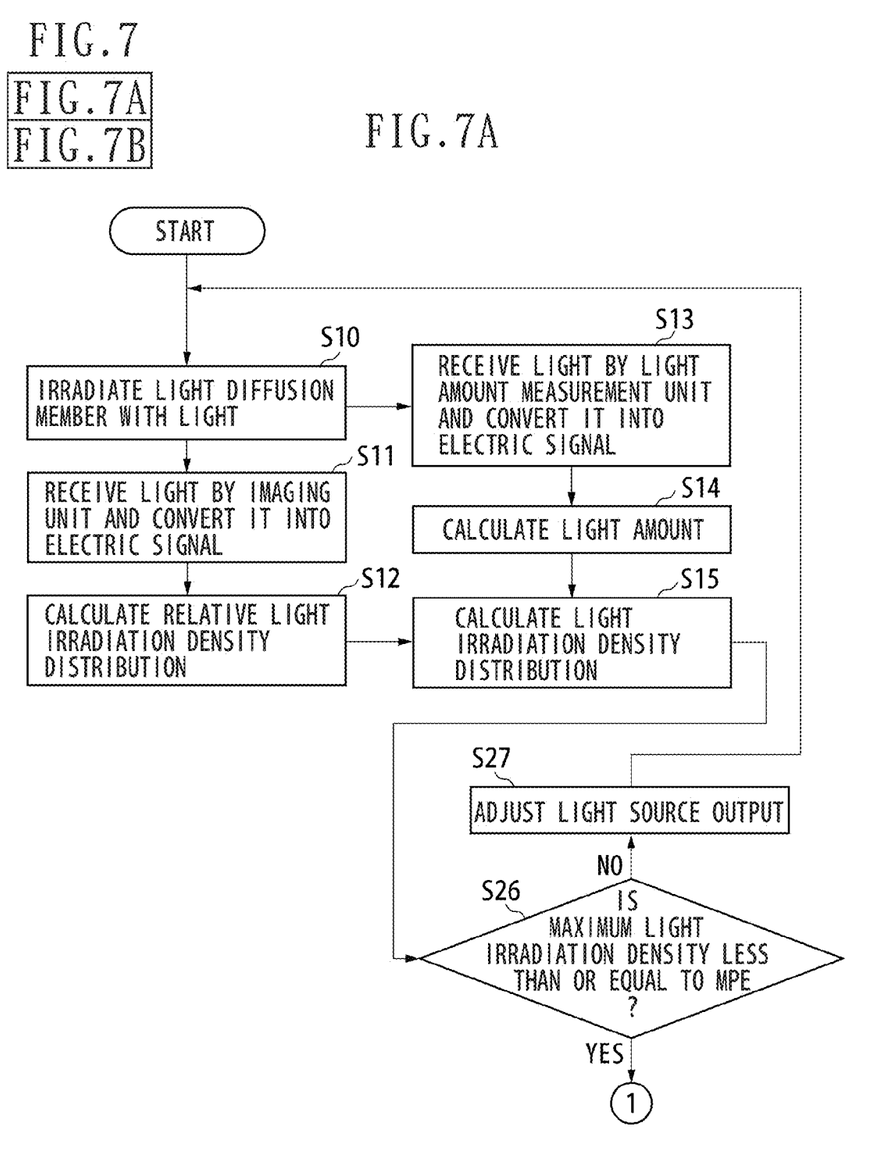
Figure 7B:
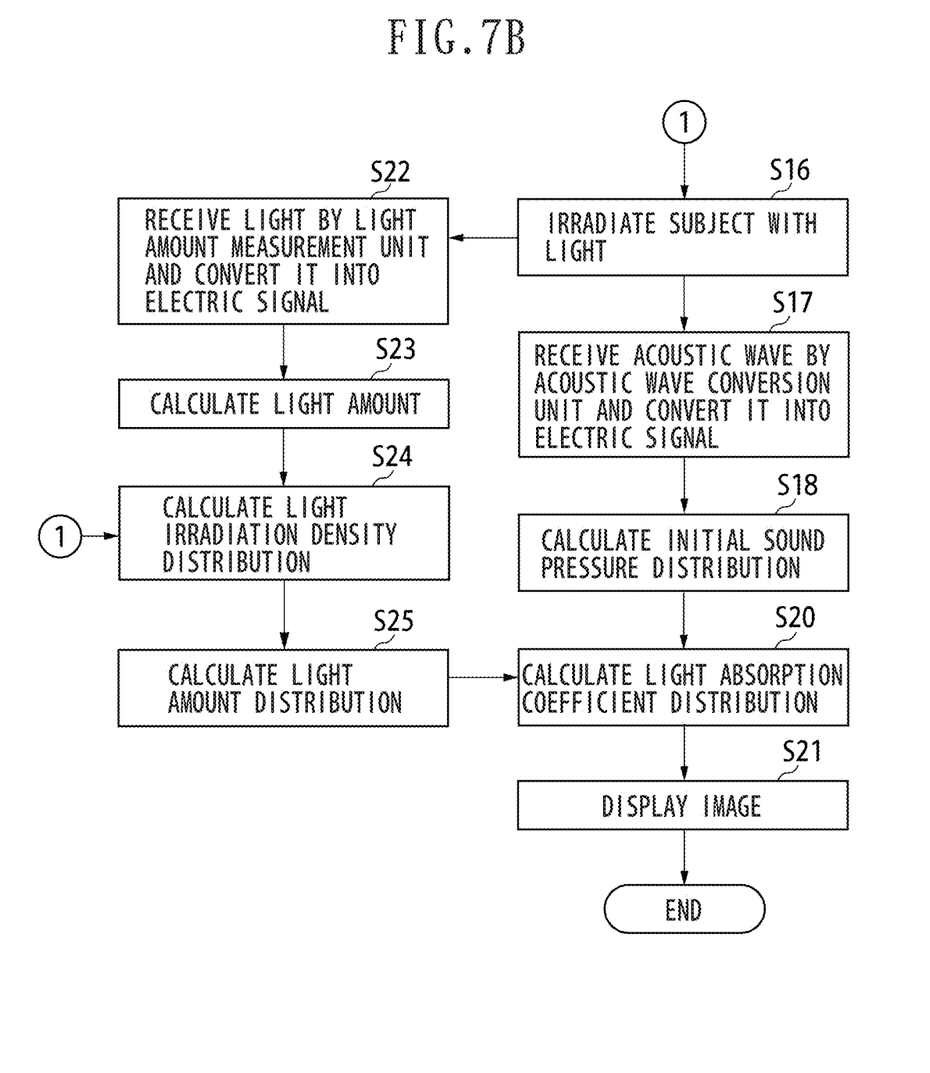

Referring to FIG. 7 (7A and 7B), the operation of the photoacoustic imaging apparatus according to the exemplary embodiment will be described. First, the processing of steps S10 to S15, step S26, steps S16 to S18, and if necessary, the processing of step S27 is performed similarly to the third exemplary embodiment.

Then, similar to the second exemplary embodiment, in step S22, when light irradiation to the subject 20 is performed, a part of the light 11 (reference light 17) is received by the light amount measurement unit 18, and the reference light 17 is converted into an electric signal. Then, the processing of steps S23 to S25 described in the second exemplary embodiment is performed. The relative light irradiation density distribution used in step S24 is the relative light irradiation density distribution calculated in step S12 in the determination that the maximum light irradiation density is less than or equal to the MPE in step S26.

In step S20, using the initial sound pressure distribution calculated in step S18 and the light amount distribution calculated in step S25, the processing unit 19 calculates light absorption coefficient distribution. Finally, the processing unit 19 generates image data of the light absorption coefficient distribution calculated in step S20. In step S21, the image data is displayed by a display device (not illustrated).

The processing for determining whether the maximum value of the light irradiation density distribution calculated in step S24 according to the present exemplary embodiment is less than or equal to the MPE can be performed between step S24 and step S25. In such a case, whether the maximum value of the light irradiation density distribution does not exceed the MPE can be monitored. In a case where the maximum value of the light irradiation density distribution exceeds the MPE, the input of the electric power to the light source 10 may be stopped. With the configuration, its safety can be increased.

Example 5

Figure 8A:
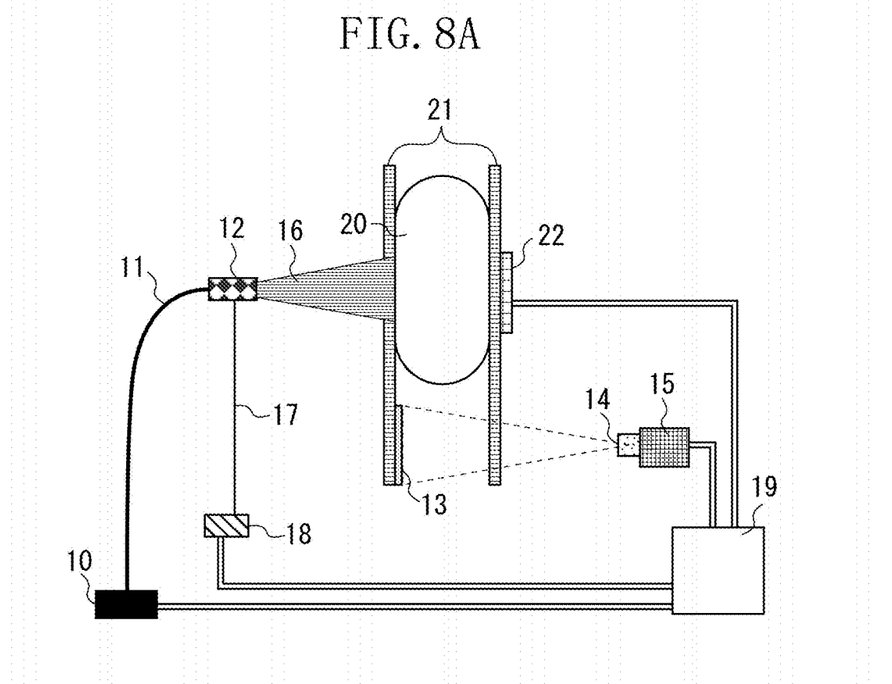
FIGS. 8A and 8B are schematic views illustrating an example configuration of a photoacoustic imaging apparatus according to a fifth exemplary embodiment of the present invention.
Figure 8B:
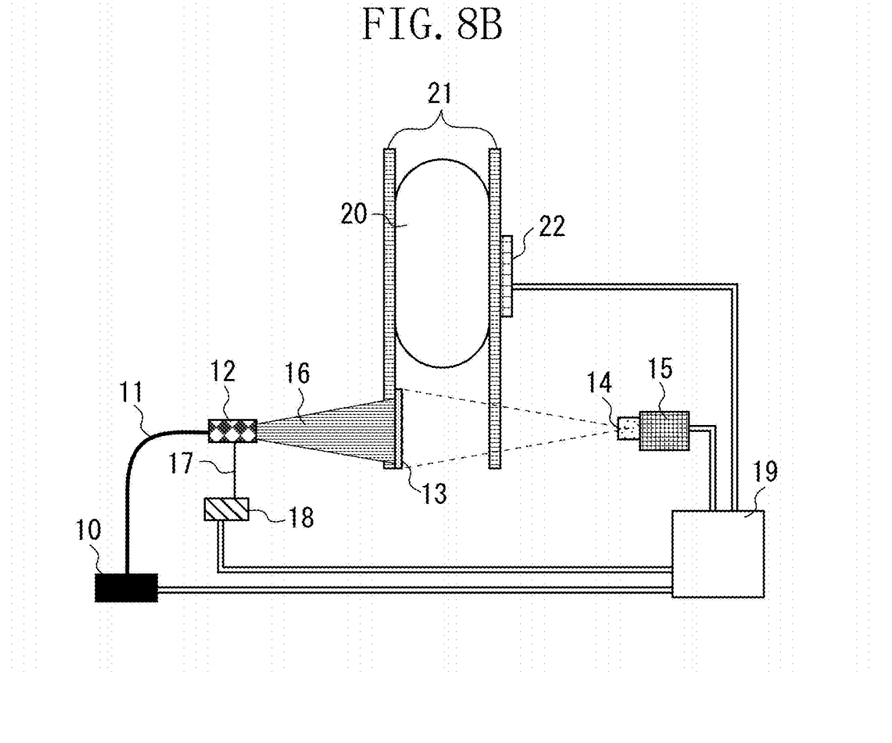

FIGS. 8A and 8B are schematic views illustrating an example configuration of a photoacoustic imaging apparatus according to a fifth exemplary embodiment. The photoacoustic imaging apparatus differs from that in the first exemplary embodiment in that the light diffusion member 13 is provided in a part of the holding members 21. With the configuration, in a state where the holding members 21 are holding the subject 20, the light diffusion member 13 is arranged to a position substantially equal to the position of the surface of the subject 20, that is, to a position substantially equal distances from the optical system 12 to the surface of the subject 20 and from the optical system 12 to the light diffusion member 13.

With the configuration, relative light irradiation density distribution calculated from a diffusion pattern that appears by irradiating the light onto the light diffusion member 13, and light irradiation density distribution becomes similar to distribution obtained by actually irradiating the surface of the subject 20 with the light. Accordingly, the light amount distribution in the subject 20 and the light absorption coefficient distribution can be more accurately calculated.

The optical system 12 is movably configured to irradiate the light diffusion member 13 and the subject 20 with the light at different positions. Specifically, the optical system 12 includes a scanning mechanism for scanning along a side of the plane, which does not hold the subject 20, of the holding members 21. The light source 10 and the light amount measurement unit 18 may also be movably configured. In the processing according to the exemplary embodiment, the processing described in the first to fourth exemplary embodiments can be performed. However, the light irradiation to the light diffusion member 13 in step S10 differs in that the light irradiation is performed in a state where the subject 20 is being held by the holding members 21.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-104300 filed Apr. 28, 2010, which is hereby incorporated by reference herein in its entirety.

The invention claimed is:

1. A photoacoustic imaging apparatus comprising:
   a light source configured to emit first light and second light;
   a light diffusion member;
   a light amount measurement unit configured to measure a light amount of a part of the first light emitted from the light source;
   an acoustic wave conversion unit configured to receive an acoustic wave generated by irradiating a subject with the first light and convert the acoustic wave into an electric signal;
   a processing unit configured to generate image data based on the electric signal; and
   an imaging unit configured to capture an optical pattern of the second light on the light diffusion member, the optical pattern being generated by irradiating the light diffusion member with the second light,
   wherein the first light is light emitted by the light source to irradiate the subject, and the second light is light emitted by the light source to irradiate the diffusion member without irradiating the subject,
   wherein the processing unit is configured to calculate relative light irradiation density distribution of the second light based on the optical pattern of the second light captured by the imaging unit,
   wherein the processing unit is configured to calculate light irradiation density distribution of the first light based on the relative light irradiation density distribution of the second light calculated by the processing unit and the light amount of the part of the first light measured by the light amount measurement unit,
   wherein the processing unit is configured to calculate light amount distribution of the first light in the subject based on the light irradiation density distribution of the first light calculated by the processing unit, and
   wherein the processing unit is configured to generate image data of a light absorption coefficient distribution in the subject based on the light amount distribution of the first light in the subject and the electric signal.

2. The photoacoustic imaging apparatus according to claim 1, wherein the processing unit is configured to control the light source so that a maximum value of the light irradiation density distribution of the first light is less than or equal to a maximum permissible exposure amount for the subject.

3. The photoacoustic imaging apparatus according to claim 1, wherein the light source is a laser generator.

4. The photoacoustic imaging apparatus according to claim 1, further comprising a holding members configured to hold the subject by contacting the subject,
wherein the light diffusion member is arranged on the holding member.

5. The photoacoustic imaging apparatus according to claim 1, further comprising:
an optical system configured to lead light from the light source to the subject and to the light diffusion member.

6. The photoacoustic imaging apparatus according to claim 1, wherein the light diffusion member is configured to be removed from the photoacoustic imaging apparatus.

7. The photoacoustic imaging apparatus according to claim 1,
wherein the light amount measurement unit includes one of an optical sensor, a thermal sensor, and a pyroelectric sensor.

8. The photoacoustic imaging apparatus according to claim 1,
wherein the imaging unit includes plural elements configured to detect light.

9. The photoacoustic imaging apparatus according to claim 1,
wherein a thickness of the light diffusion member is from 0.1 mm to 1.0 mm.

10. A photoacoustic imaging method comprising:
irradiating a subject with first light;
measuring a light amount of a part of the first light;
converting an acoustic wave generated by the irradiating the subject with the first light into an electric signal;
irradiating a light diffusion member with second light, wherein the first light is light emitted by a light source to irradiate the subject, and the second light is light emitted by the light source to irradiate the diffusion member without irradiating the subject;
capturing an optical pattern of the second light generated on the light diffusion member;
calculating relative light irradiation density distribution of the second light based on the optical pattern of the second light;
calculating light irradiation density distribution of the first light based on the relative light irradiation density distribution of the second light and the light amount of a part of the first light,
calculating light amount distribution of the first light in the subject based on the light irradiation density distribution of the first light, and
generating light image data of absorption coefficient distribution in the subject based on the light amount distribution of the first light in the subject and the electric signal.

11. The photoacoustic imaging method according to claim 10, further comprising determining whether a maximum value of the light irradiation density distribution of the first light is less than or equal to a maximum permissible exposure amount for the subject.

12. The photoacoustic imaging method according to claim 11, further comprising controlling the light source that emits the first light so that the maximum value of the light irradiation density distribution of the first light becomes less than or equal to the maximum permissible exposure amount if the maximum value of the light irradiation density distribution of the first light is not less than the maximum permissible exposure amount for the subject.

13. The photoacoustic imaging method according to claim 10, further comprising controlling a light source that emits the first light so that a maximum value of the light irradiation density distribution of the first light is less than or equal to a maximum permissible exposure amount for the subject.

* * * * *